United States Patent [19]

Fleischle

[11] Plant 4,522

[45] Apr. 22, 1980

[54] DISTINCT VARIETY OF STREPTOCARPUS NAMED GRETA

[75] Inventor: Gerhard Fleischle, Vaihingen, Fed. Rep. of Germany

[73] Assignee: Oglevee Associates, Inc., Connellsville, Pa.

[21] Appl. No.: 958,831

[22] Filed: Nov. 8, 1978

[30] Foreign Application Priority Data

Jul. 7, 1978 [DE] Fed. Rep. of Germany ..... S.T.C.3

[51] Int. Cl.[2] ..... A01H 5/00

[52] U.S. Cl. ..... Plt./68

[58] Field of Search ..... Plt./68

*Primary Examiner*—Robert E. Bagwill
*Assistant Examiner*—James R. Feyrer
*Attorney, Agent, or Firm*—Webb, Burden, Robinson & Webb

[57] ABSTRACT

A new variety of Streptocarpus plant is characterized by its purplish blue flower having dark violet striping in the throat. It has large flowers, long permanence and is generally nonfertile.

1 Drawing Figure

BACKGROUND OF THE NEW PLANT

The present invention comprises a new and distinct cultivar of *Streptocarpus x hybridus* known by the varietal name Greta, formerly named Helle Glocke. The new cultivar is an irradiated sport of Nadia whereas Nadia is a cross between the seed parent Wiesmoor Blue and the pollen parent Constant Nymph.

The new cultivar is basically the same color as Nadia and has the same shape of bloom. However, the new cultivar has more blooms per plant and the blooms last substantially longer than for Nadia.

The new cultivar was discovered in 1975 in Vaihingen, Federal Republic of Germany; was first asexually reproduced by cuttings in Vaihingen, Federal Republic of Germany; and has been repeatedly asexually reproduced by cuttings at Oglevee Floral Company in Connellsville, Pa. It has been found to retain its distinctive characteristics through successive propagations.

The new cultivar, when grown in a greenhouse in Connellsville, Pa., has a response time of eight weeks from a plantlet (a well rooted young plant in a five centimeter pot) to a flowering plant in a ten centimeter pot.

DESCRIPTION OF THE DRAWING

The accompanying drawing illustrates the new cultivar, the color being as nearly true as possible with color illustrations of this type.

BACKGROUND OF THE NEW PLANT

The following detailed description sets forth the characteristics of the new cultivar. The data which defines these characteristics were collected from asexual reproductions carried out by the Oglevee Floral Company in Connellsville, Pa. The plant history was taken on eight week plants blossomed under natural light in a greenhouse and color readings were taken indoors under 100 foot candles of cool white fluorescent light. Color references are primarily to the R.H.S. color chart of the Royal Horticultural Society of London. Some color reference is to Exotica III and such reference is duly noted.

Botanical classification: Gesneriaceae (family); *Streptocarpus x hybridus* (genus x species).

Flower:

*Fully expanded.*—Six centimeters.

*Borne.*—In clusters of one to six flowers per flower stalk above the foliage. Flower stalks arise from mid-rib of each leaf.

*Stems.*—Single, long and pubescent.

*Form.*—Funnel formed in an umbel.

*Permanence.*—Long lasting 21 to 25 days.

Color:

*Front of petals.*—Fan 2 violet group 88-A.

*Throat.*—Fan 1 yellow group 3-B with a plurality of stripes, Fan 2 violet group 83-A, extending into the center of the petals.

*Base of petals.*—Fan 2 purple group 76-D.

*Reverse of petals.*—Fan 2 violet group 88-C.

*Tonality from a distance.*—Purplish blue and dark violet striping in throat (Exotica III).

*Discoloration.*—Insignificant.

Petals:

*Texture.*—Velvet.

*Appearance.*—Individually lobed and smooth margin.

*Arrangement.*—Regularly united into an elliptical form.

*Persistance.*—Lives for 21 to 25 days and remains on plant in dry form until picked.

*Fragrance.*—None.

Reproductive organs:

*Anthers.*—Two per flower and interconnected.

*Filament.*—Two and one-half centimeters initiating from the base of petal and extending to the anther.

*Pollen.*—Generally nonfertile.

*Style.*—Extends from tip of ovary one centimeter and terminates in a flattened stigma.

*Ovaries.*—Long and narrow, one and one-half millimeters in diameter and one and one-half centimeters long.

Plant:

*Form.*—Leaves rosulete from a crown at the soil line.

*Growth.*—A spreading, free flowing habit with leaf bases being acute.

*Height from soil line.*—15 to 20 centimeters.

*Spread.*—35 to 40 centimeters.

Foliage:

*Top side.*—Fan 3 green group 137-B.
*Size.*—Approximately 20 centimeters in length and 5 to 10 centimeters in width at widest point.
*Quantity.*—10 to 15 leaves.
*Shape.*—Oblanceolete.
*Ribs and veins.*—Pinnate.
*Rib and vein color.*—Fan 3 green group 138-B.

*Margin.*—Ruffled margin with crenate serrations.
*Underside.*—Fan 4 greyed green group 193-A.
*Stipules.*—None.

I claim:

1. A new and distinct variety of Streptocarpus substantially as herein shown and described.

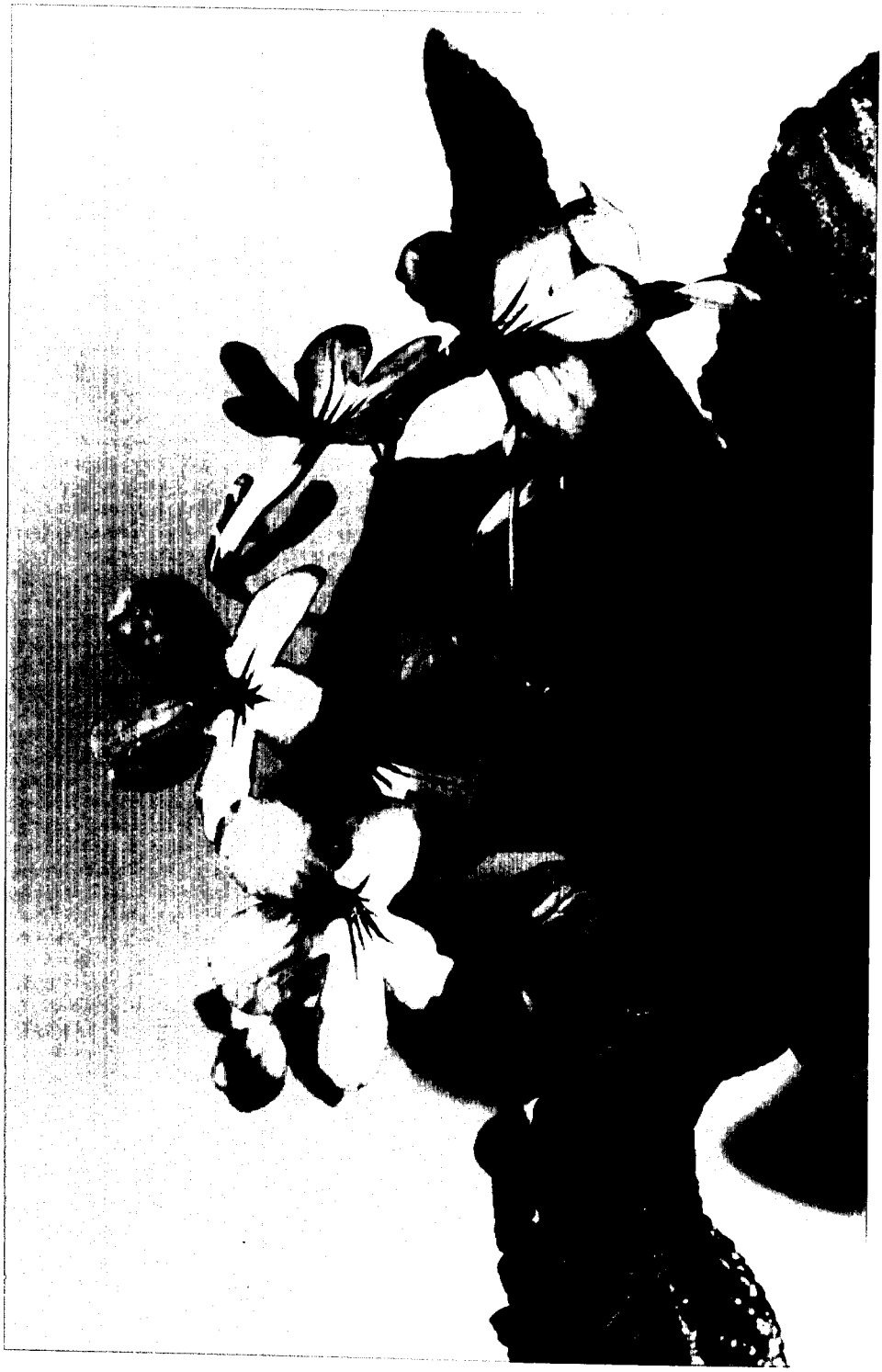

* * * * *